United States Patent [19]

Wilke et al.

[11] 4,359,533

[45] Nov. 16, 1982

[54] FERMENTATIVE ALCOHOL PRODUCTION

[75] Inventors: Charles R. Wilke, El Cerrito; Brian L. Maiorella; Harvey W. Blanch, both of Berkeley, all of Calif.; Gerald R. Cysewski, Kennewick, Wash.

[73] Assignee: The United States of America as represented by the Department of Energy, Washington, D.C.

[21] Appl. No.: 210,485

[22] Filed: Nov. 26, 1980

[51] Int. Cl.$^3$ .............................................. C12P 7/06
[52] U.S. Cl. .................................... 435/161; 435/162; 203/19; 203/91; 203/DIG. 13; 203/DIG. 6
[58] Field of Search ............... 435/161, 162, 163, 164, 435/165; 203/19, DIG. 13, DIG. 11

[56] References Cited

U.S. PATENT DOCUMENTS 1,676,700  7/1928  Lewis ..................................... 203/19

OTHER PUBLICATIONS

Cysewski, Rapid Ethanol Fermentation Using Vacuum and Cell Recycle, Biotechnology and Bioengineering, vol. XIX, pp. 1125–1143, 1977.
Maiorella et al., Rapid Ethanol Production via Fermentation AICHE meeting, Nov. 27, 1979.

*Primary Examiner*—Raymond N. Jones
*Assistant Examiner*—John E. Tarcza
*Attorney, Agent, or Firm*—Harold M. Dixon; Roger S. Gaither; Richard G. Besha

[57] ABSTRACT

An improved fermentation process for producing alcohol which includes the combination of vacuum fermentation and vacuum distillation. Preferably, the vacuum distillation is carried out in two phases, one a fermentor proper operated at atmospheric pressure and a flash phase operated at reduced pressure with recycle of fermentation brew having a reduced alcohol content to the fermentor, using vapor recompression heating of the flash-pot recycle stream to heat the flash-pot or the distillation step, and using "water load balancing" (i.e., the molar ratio of water in the fermentor feed is the same as the molar ratio of water in the distillation overhead).

10 Claims, 1 Drawing Figure

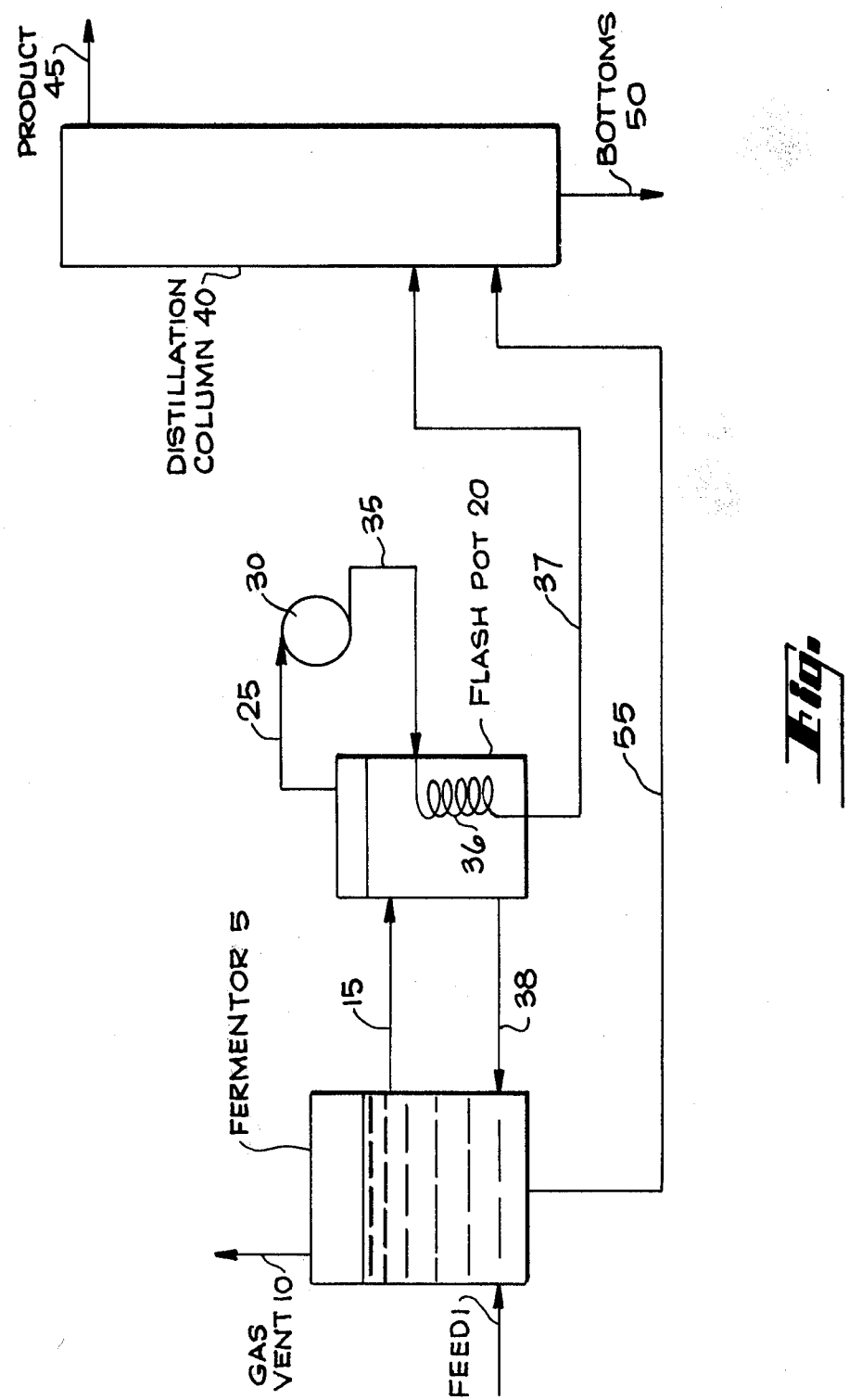

FERMENTATIVE ALCOHOL PRODUCTION

BACKGROUND OF THE INVENTION

The United States Government has rights in this invention pursuant to Contract No. W-7405-ENG-48 between the United States Department of Energy and the University of California.

FIELD OF THE INVENTION

This invention relates to the fermentative production of alcohol, particularly ethyl alcohol.

DESCRIPTION OF PRIOR ART

Decreasing supplies of fossil fuels have made it necessary to investigate alternative sources of energy. Cellulosic matter in biomass such as agriculture and wood products constitute a potentially significant national energy resource. Enormous quantities of such products in the form of waste are available, and additional supplies can be grown specifically for conversion to energy bearing products. It has been proposed to convert such wastes, or other cellulosic materials, to glucose by enzymatic hydrolysis and subsequently ferment the glucose to ethanol, a liquid fuel. However, the more traditional conversion of natural sugars can be used and will undoubtedly be a substantial source of raw materials to make fermentation products such as alcohol by the present invention.

One major problem encountered with fermentative production of alcohol is that the alcohol is self-inhibiting. In more detail, the desired alcohol product has an inhibiting effect on the yeast thereby severely limiting the ultimate alcohol concentration and therefore quantity produced.

Traditional fermentation has been carried out in a batch form of operation. Generally, a batch is terminated when a maximum of alcohol is produced due to the self-inhibiting effect on the reaction. Batch operation requires very large fermentors which must be shut down and cleaned after completion of each batch. The process is thus capital and labor intensive. In addition the energy required in the distillation is relatively high and today prohibitively so.

Continuous fermentation as known and practiced in the art has some advantages over batch fermentation; however, it also has limitations and disadvantages. The flow rate in continuous fermentation is limited to the yeast growth rate because the yeast is carried away with product flow. The flow rate must be slowed commensurate with the growth rate of the yeast.

A continuous process modified to include recycle of the yeast increases the yeast concentration and the reaction rate correspondingly. The fermentors required for a particular product volume are smaller because of the increased reaction rate. However, this process requires separation of the yeast for recycle. Consequently, yeast separation in such a process generally requires centrifuging in order to avoid excess temperature levels.

Vacuum fermentation is a more recent modification which takes into consideration the fact that ethanol inhibits the yeast from functioning as a fermentation catalyst. In vacuum fermentation, sometimes called "vacuferm", the vacuum in the fermentor causes the volatile alcohol (and some water) to be boiled away during the fermentation. Alcohol concentration is thus kept relatively low in the fermentor and alcohol's inhibiting effect is thereby kept low. The increased fermentation rate which is thereby achieved by decreased alcohol concentration eliminates the need for a bleed stream for recycle of yeast. The elimination of a bleed stream from the fermentor causes the build-up of nonvolatile products (e.g. fusel oils) which are toxic to fermentation organisms. Therefore a small (i.e., smaller than in atmosphere fermentation) bleed stream to provide for elimination of nonvolatile toxic compounds is required. Yeast, of course, is recycled from such a stream to maintain a high concentration and high reaction rates. These modifications do not alter the large energy requirements for the subsequent distillation step to separate and recover the alcohol. The distillation to recover the alcohol does not change the large energy requirements of this step because of distillation phenomena and of the ethanol-water azeotropes in particular.

Examples of the vacuferm process are U.S. Pat. No. 2,440,925 to Boekeler, "Rapid Ethanol Fermentation Using Vacuum and Cell Recycle", Biotechnology and Bioengineering, 19, 1125 (1977), by Czsewski and Wilke, and "The Vacuferm Process: A new Approach to Fermentation Alcohol", Biotechnology and Bioengineering, Vol. XIX (1977), by Ramalingham and Finn. While the work of these researchers is notable their vacuferm processes suffer significant disadvantages. Among the disadvantages are: (1) the yeast's oxygen requirements can only be met by sparging relatively pure oxygen to the fermentor rather than air; and (2) all of the $CO_2$ by-product gas produced and which is taken over with the crude alcohol from the fermentor must be compressed in subsequent stages.

In U.S. Pat. No. 2,440,925, Boekeler saw the advantages of reducing the size of the vessel under vacuum. Accordingly Boekeler taught an alternative embodiment wherein the main fermentor is maintained at atmospheric pressure but a portion of the fermenting liquor is charged to a vacuum distillation column for a rough separation. The alcohol rich fraction is then distilled at atmospheric pressure. This approach requires the use of a cooling coil in the vacuum distillation to avoid elevating the temperature significantly with the results that at least part of the yeast cells would be destroyed or killed. In the process described, the distillation at atmospheric pressure consumes much more energy than a properly conducted vacuum distillation.

Vacuum distillation as practiced in the art requires that the vacuum distillation column be several times larger than one at atmospheric (eg. a diameter at vacuum of 3 times that at atmospheric). It is apparent that such has the disadvantage of requiring much greater capital investment alone without considering other factors.

It is thus clearly apparent that there is considerable room for improvements in the prior art processes for fermentative production of alcohol.

In todays energy shortage environment where alcohol is sought for use as a fuel, there is a question of whether viewed overall ethanol produced by the prior art fermentation processes results in a net energy loss or gain.

None of the previous fermentation processes is economically competitive with existing processes for ethanol production which are based on petroleum-derived raw materials. Such a situation makes it imperative in these times of energy and petroleum shortage to dramatically improve fermentative processes.

It is among the objects of the present invention to provide an improved process for producing alcohol from the fermentation of sugar and sugar-type fermentable matter.

Another object of the invention is to provide a process which increases the fermentation rate of fermentable matter to ethanol.

It is another object of the present invention to provide a process for producing ethanol in higher yields from fermentable matter.

Yet another object of this invention is to provide a process for producing ethanol which requires less energy consumption.

Still another object of this invention is to ameliorate if not obviate disadvantages of the various prior art fermentation processes to produce alcohol.

A particular object of this invention is to provide a process for producing ethanol in which the fermentation rate in the fermentation operation is accelerated, high yields of ethanol are obtained and wherein the fuel energy in the alcoholic product is greater than that consumed by the process of converting sugars to ethanol.

It is a further object to achieve enhanced fermentative production and recovery of compounds which exhibit a self-inhibiting effect in the fermentation reaction.

Other objects, advantages and novel features of the present invention will become apparent from the following detailed description.

SUMMARY OF THE INVENTION

The foregoing and other objects of the invention are accomplished by a process for producing alcohol which in brief comprises the combination of:
- a fermentation phase carried out at least in part under subatmospheric pressure to produce a fermentation brew containing alcohol, at least part of which is under reduced pressure;
- subjecting the crude alcohol fraction under reduced pressure to vacuum distillation phase to separate and recover high purity alcohol.

A broad but preferred embodiment comprises the combination of:
- conducting fermentation on fermentable matter to form alcohol at atmospheric pressure;
- subjecting a portion of said fermentation culture or beer to vacuum flash-pot conditions for removal of at least part of said alcohol to form a crude alcohol fraction under reduced pressure;
- returning said fermentation beer containing reduced alcohol content to atmospheric fermentation;
- subjecting the crude alcohol fraction under reduced pressure to vacuum distillation and recovering high purity alcohol.

Particularly advantageous embodiments include using vapor recompression heating of flash-pot fermentation beer for recycle to the atmospheric fermentation for heating at least one of the flash-pot or distillation steps, and "water load balancing" wherein the molar ratio of alcohol to water in the overhead from the flash-pot is substantially the same as the molar ratio of sugar to water in the feed to the fermentor such that no water need be recycled from the heated distillation bottoms to avoid fermentor water depletion.

A BRIEF DESCRIPTION OF THE DRAWING

The FIGURE is a schematic flow diagram illustrating the fermentative production of alcohol incorporating the various principal advantageous features of this invention.

DESCRIPTION OF THE PREFERRED EMBODIMENTS

Having now described the invention in broad and general terms, the understanding of same will be aided by the detailed discussion which follows.

The principal features or parameters of the fermentation of the present invention include the fermentation catalyst, the temperature, the pressure, and the alcohol concentration in the fermentor. Many of these features are known in the art and are employed in the same ranges in some embodiments of the present invention. Before proceeding further to discuss these features in great detail and quantitatively, it will be found helpful to discuss the general trends of variables and the interdependence or interrelationship of some features.

The fermentation catalyst is very sensitive to temperature. The catalyst growth rate and the fermentation rate are slow at low temperatures. On the other hand when the temperature is elevated above a narrow range the catalyst is permanently deactivated or destroyed. The pressure varies directly with temperature but is to be kept as high as possible for reasons discussed elsewhere herein. The alcohol product concentration is of course to be as high as possible commensurate with the tolerance of the catalyst.

The catalysts which can be employed in the present invention are any of those which can be used in fermentation processes for producing alcohol from sugars. Illustrative examples of suitable catalysts known in the art are yeast, *Saccharomyces cereviciae anamensis, Clostridium thermosaccharolyticum,* (b) and *Fusarium oxysporum.* We prefer yeast for a number of reasons but several other fermentation catalysts produce good results on sugar-type products or products containing sugar.

The feed material for the alcohol is a sugar type (i.e. glucose, fructose, etc.) containing product. The sugar may be either a refined, partially refined or a natural one such as those found in the fruits of crop plants. Examples are corn, beets, etc. The fruits can be fruit crops per se such as peaches, pears, grapes, etc. The sugar can be a sugar solution or a sugar containing material but preferably is a solution or essentially a solution. Accordingly, a sugar containing material is preferably pretreated to remove the sugar from nonsugar fiber, tissue, pulp, etc. Also, the sugar may be a hydrolyzed cellulosic biomass such as wood or agricultural by-products. The foregoing is not exhaustive but rather illustrative of raw materials or feed known in the art to be suitable for use in fermentation processes to make alcohol.

For completeness the hydrolyzation of cellulosic biomass is briefly discussed here. The biomass such as wood or bagasse is treated with cellulose enzymes at atmospheric pressure and a temperature of about 45° C. for approximately 24 to 48 hours to produce a fermentable glucose containing product.

The fermentation step itself is carried out in the general range of about 10°–100° C. Preferably, the temperature is in the range of about ambient (i.e. about 18°–20° C.) to a temperature below which the catalyst is significantly adversely affected. For bacterium, the foregoing described temperature in some cases can be as high as about 100° C., but more usually is not above about 75° C. Temperatures below about 10° C. can be used but the reaction rate normally is too slow. Ambient temperature is the practical lower limit for economic reasons. Yeast is the preferred organism as catalyst and a lower temperature in the range of about 15° C. to 35° C. is preferred when yeast is employed. The temperature should never exceed about 40° C. with yeast as the organism is killed and its effectiveness is destroyed at higher temperatures.

The pressure of the fermentation can be subatmospheric on the order of about 50 to 500 mm Hg. Usually pressures of about 50 to 150 mm Hg will be preferred. The volatile products from the fermentor comprising crude alcohol is charged to a vacuum distillation to separate and recover the alcohol. However, more preferred to the foregoing is an embodiment wherein atmospheric pressure is used in the fermentor proper and a stream from the fermentor is fed to a flash-pot operated under reduced pressures on the order discussed above to remove a crude alcohol stream which is then vacuum distilled.

By the combination of vacuferm or flash-fermentation ("flashferm") with vacuum distillation a synergistic savings in energy requirements is obtained.

The unexpected synergerism between vacuum (or flash) fermentation and vacuum distillation will be made clear by considering the following:

(1) the deficiencies of ordinary continuous fermentation combined with ordinary atmospheric pressure distillation, (2) the deficiencies of vacuum (flash) fermentation and vacuum distillation practiced separately, (3) the superior energy efficient operation when the two processes of vacuum or flash fermentation and vacuum distillation are used in synergistic combination to produce 95 wt% ethanol, as compared to (1) and (2).

Ordinary continuous fermentation of glucose sugar by yeast microorganisms can be used in combination with atmospheric distillation to produce 95 wt% ethanol product. Fermentation productivity is very low (typically 10 gm ethanol produced per liter of fermenter volume per hour). The fermentor beer product fed to distillation (after centrifugal removal of yeast) typically contains 5 wt% ethanol. Ordinary atmospheric pressure distillation (when conducted efficiently) will require $7.0 \times 10^6$ Joules per liter of product energy input to produce 95 wt% product from the 5 wt% beer feed.

Vacuum (or flash) fermentation may be combined with ordinary distillation to produce 95 wt% ethanol. Fermentor productivity is greatly increased (to 8° gm ethanol per liter hrs typically). A 20 wt % ethanol beer feed is sent to the distillation column (14 wt % for flash fermentation). It would then be expected that the final distillation and hence energy requirement, would be far less than for the combination of ordinary fermentation and atmospheric distillation. This would be expected based on the much more concentrated beer feed than in ordinary continuous fermentation which would enable a lower reflux ratio. Reflux ratio refers, of course, to product taken out at head of column to that condensed and cycled back down through the column. This return flow is necessary to affect the separation—large return flows being required for more of difficult separations. This expected savings is not realized. The distillation energy is $6.79 \times 10^6$ Joules per liter of product distilled (The slight energy savings comes because less water must be warmed in the column feed preheater). In addition, $1.26 \times 10^6$ Joules per liter, extra, energy is consumed by the vacuum fermentation vacuum compressors ($1.07 \times 10^6$ Joules per liter for flash fermentation).

Ordinary continuous fermentation can be used in combination with vacuum distillation to produce 95 wt % ethanol product. Fermentor productivity is low. The distillation energy requirement to concentrate the 5 wt % fermentor beer feed to 95 wt % is virtually identical to the distillation requirement if atmospheric pressure distillation is used. Because vacuum distillation is run at lower temperatures than atmospheric pressure distillation, there is some incentive to use vacuum distillation if recoverable "waste" heat is available in the plant. This advantage is ordinarily nullified, however, by the tremendous increase in distillation column diameter for vaccuum stills as compared to ordinary atmospheric pressure stills.

Vacuum (or flash) fermentation can be used in combination with vacuum distillation to produce a 95 wt % ethanol product. Under correct conditions of fermentation, very high fermentor productivities are achieved. Further, the final distillation of the 20 wt % ethanol product from vacuum fermentation (14 wt % from flash fermentation) by a vacuum distillation operated under the correct conditions is reduced to only $2.50 \times 10^6$ Joules per liter of ethanol product. Even when the vacuum fermentor compressor energy requirement of $1.26 \times 10^6$ Joules/liter is added, a total energy saving of 46% (48% for flash fermentation with its smaller compressors) results are compared to conventional continuous fermentation and atmospheric distillation.

The unexpected synergy between vacuum (or flash) fermentation and vacuum distillation is now apparent. Vacuum (or flash) fermentation, in combination with atmospheric distillation offers no substantial energy savings. When vacuum (or flash) fermentation is properly combined with vacuum distillation, an energy savings of almost 50% is achieved as compared to conventional practice. Desirable synergistic effects extend also to distillation equipment size reduction. If vacuum distillation is used in combination with ordinary fermentation, proper still design practice calls for an approximate doubling of the still diameter as compared to an atmospheric pressure still, to maintain proper vapor flow linear velocities (the specific volume of vapors is greatly increased under vacuum). If vacuum (or flash) fermentation is used in combination with vacuum distillation, the expected large increase in distillation column diameter over atmospheric distillation, is not required. For the suggested case of a column, producing 10,000 kg/hr at 95 mm Hg pressure, the required column diameter for proper operation is 11 ft, only a 10% increase over the size of an atmospheric pressure column operating to purify the same amount of ethanol product.

The special synegism between vacuum (or flash) fermentation, and vacuum distillation can be explained in terms of the complex theory of distillation. For a two component "ideal" system the required ratio (and hence, energy) for distillation to a fixed product concentration is set by a feed limitation and decreases continuously as feed concentration is increased. Thus, for an "ideal" system, the concentration effect of vacuum (or flash) fermentation would reduce the final distillation energy requirement. Many common systems behave nearly "ideally", the ethanol/water system (and all other systems which form constant boiling azeotropic mixtures) behaves substantially different from "ideal".

For such systems, another limitation—a high concentration pinch associated with the azeotrope may become limiting and necessitate high required reflux ratio (and hence high energy inputs) for distillation. Increases in the feed concentration do not reduce the required reflux ratio as this must be maintained high as necessitated by the high concentration pinch.

For the ethanol/water system (and other systems forming azeotropes) the shift in the azeotrope at reduced pressure can analyze the high concentration pinch limitation to achieve a product concentration near the atmospheric pressure azeotrope concentration less taxing. If this limitation was controlling before pressure reduction, then reflux ratio and hence, energy input) may be reduced by lowering pressure.

For ordinary continuous fermentation combined with simple atmospheric distillation, both the feed and high concentration pinches are simultaneously limiting. The use of vacuum (or flash) fermentation makes the feed limitation less taxing, but no reduction is required in reflux ratio or distillation energy results, as the high concentration limitation is still in effect. Use of the vacuum distillation with ordinary continuous fermentation relieves the high concentration pinch limitation, but the feed limitation still necessitates high reflux and, hence, high energy input.

By combining vacuum (or flash) fermentation with vacuum distillation, both the feed and high concentration pinch limitations are made simultaneously less taxing. For typical conditions of 20 wt% ethanol feed concentration from the vacuum fermentor, and 95 mm Hg distillation column pressure, the required reflux ratio is reduced from 8.00 (for an ordinary atmospheric pressure column, in a vacuum distillation column fed the dilute beer from an ordinary fermentor) to only 2.56. The column diameter is not greatly increased by vacuum operation since, with a low reflux ratio, the internal column gas and liquid flow rates are greatly reduced. A 48% energy reduction is achieved.

As mentioned above the fermentation at atmospheric pressure coupled with a vacuum flash-pot is an advantageous and preferred embodiment of the present invention. The reasons for this are that with a flash-pot, the vessel required to be kept under vacuum is much smaller. The oxygen requirements of the catalyst in the fermentor can be supplied with air instead of oxygen. $CO_2$ by-product gas can be vented from the fermentor to avoid subsequent processing without loss of significant alcohol product. In this way the alcohol concentration in the feed stream from the flash-pot to the vacuum distillation can be as high as about 15%. In turn the fermentation brew or liquor from the flash-pot has an enriched catalyst concentration, and increases the catalyst concentration in the fermentor when returned thereto. These factors provide for a high reaction rate and high through-put so that the equipment is relatively small in size.

The small concentration of sugar in the feed can vary over a wide range but typically is as high as is practical technically. The water content is more critical in that by means of controlling the water content of the feed relative to the water flashed-off in the fermentors or flash pot (depending on the embodiment used in the fermentaion stage). The pressure and temperature are important variables in respect to the various aspects of the process water feature as will be exaplained.

At any given temperature and pressure the ratio of alcohol to water going overhead from the fermentation stage is fixed by the phase equilibrium. For example, according to the prior art processes, a 25% sugar solution fed to the fermentor will result in a ratio of alcohol to water going overhead of 1/9 (one to nine) due to equilibrium phenomena. At the same time stoichiometry phenomena results in ½ pound of ethanol formed for each pound of sugar (i.e. glucose) fed. Then based on mass balance 3 (three) pounds of water must be fed into the fermentation stage for each pound of sugar and 3 (three pounds) of water must be taken out for the fermentation stage for each ½ (one-half) pound of ethanol taken over. Alternatively stated, the ratio of ethanol to water which must leave the fermentation stage is 1/6 (one to six) and not 1/9 (one to nine) as required by equilibrium.

In order to achieve the 1/6 ratio discussed above water must be added. Typically the additional water is obtained by recycling water from the bottom of the distillation stage. Of course, the recycled water from the distillation column requires cooling before charging to the fermentor. By contrast to the prior art practice in the present invention using water-load balancing, overhead compressor(s) are used to control the pressure so as to maintain the ratio of alcohol to water. By controlling the ratio of alcohol to water at such a point the amount of water leaving the fermentation stage is controlled so that it is substantially equal to the amount of water fed to the fermentation stage as sugar solution. In this way large quantities of water are not unnecessarily heated in the distillation only to be subsequently cooled for recycling through the process. Generally speaking the more concentrated solutions of sugars on the order of at least about 20–50% by weight are preferred. However, at concentrations of about 50% and higher they are quite viscous making processing and handling in general difficult. Accordingly, concentrations above 50% normally will not be employed. For water load balancing other operating conditions are usually adjusted in such cases to provide for a relatively small water requirement in the feed but sufficient for relatively easy handling of the sugar solution.

DETAILED DESCRIPTION OF THE DRAWING

In order to facilitate understanding the invention and particularly on a continuous operation basis, a detailed description with reference to the drawing follows.

A sugar solution of about 25 weight % concentration is fed at a rate of about $8.75 \times 10^4$ kg per hour through line 1 to fermentor 5 which contains about 80 gm/liter of yeast as catalyst. The fermentor is operated at about 30° C. and atmospheric pressure. The $CO_2$ gas generated is conveniently vented through line 10 for removal from the fermentor and the process. Fermentation brew or liquor is maintained for an average residence or fermentation time of about 5 hours and withdrawn through line 15 at a rate of about $7.5 \times 10^5$ kg/hr. The fermentation brew containing about 3.5 weight % alcohol is then charged to the flash pot 20 operated at a temperature of about 30° C. and a reduced pressure of about 50 mm Hg. The nonvolatized liquid in flash pot 20 containing a reduced alcohol content and enriched yeast content is recycled to fermentor 5 through line 38. Crude alcohol flashed overhead contains about 14% by weight of alcohol which is passed through line 25 to compressor 30 where it is partially compressed to about 150 mm Hg. The partially compressed stream from compressor 30 is passed through line 35 to coil 36 where it is at least partially condensed. Condensate and gas are then passed through line 37 where it is charged to a distillation column 40 operated at a partial pressure of about 150 mm Hg. Alcohol of about 95% purity by weight is taken over through line 45 and recovered in conventional equipment not shown. The bottoms comprising fusel oils and other nonvolatiles are withdrawn through line 50 at the bottom of the column.

A small bleed stream 55 of heavy (e.g. high molecular weight) material is taken from the bottom of the fermentor 5 and charged to the distillation column 40 for recovery of desired alcohol then the remainder or residual of this stream is removed from the distillation column as bottoms through line 50.

The description herein has been directed to the fermentative production of alcohol to facilitate the description and understanding; however, it should be fully understood that the advantages of the invention are also applicable to any fermentation process wherein the product(s) is/are not only volatile but azeotrope(s) with other compounds in the fermentaion beer, the azeotropes "shifts up" (i.e., distills at a higher concentration of the desired fermentation product than at atmospheric pressure) and the advantages especially obtain when the product(s) are self-inhibiting.

While particular embodiments of the invention have been described, it will be understood, of course, that the invention is not limited thereto, since many modifications may be made; and it is therefore contemplated to cover by the appended claims any such modifications as fall within the true spirit and scope of the invention.

We claim:

1. An improved fermentation process for producing alcohol which comprises the steps of:

conducting a fermentation phase at least in part under subatmospheric pressure at a temperature and for a period of time sufficient to produce a fermentation brew containing alcohol and a crude alcohol fraction;

and subjecting said crude alcohol fractin to a vacuum distillation phase to separate and recover high purity alcohol.

2. A process according to claim 1 wherein said fermentation phase is carried out in at least two vessels one a fementor which is operated at atmospheric pressure and the second is operated as a flash-pot for removal of at least part of said alcohol to form a crude alcohol fraction; and recycling the fermentation brew from said flash-pot to said fermentor.

3. A process according to claim 2 wherein the fermentation phase is operated at a temperature in the range of about 10° to 100° C.

4. A process according to claim 2 wherein the fermentation catalyst is yeast and the temperature in the fermentation phase is in the range of about ambient to 40° C.

5. A process according to claim 4 wherein the temperature of the fermentation phase is in the range of about 25° to 35° C.

6. A process according to claims 3 wherein vapor recompression of the overhead products from the flash-pot or fermentor is employed to provide heat for vaporization of liquid in the flash-pot or fermentor.

7. A process according to claim 6 wherein the vapor recompressed stream is passed through a heat exchange device in the fermentation brew in said flashpot to recover heat of recompression and to cool said recompressed stream to at least partially condense said stream to a liquid.

8. A process according to claims 1, 2, 3, 4, 5, or 7 wherein the fermentation phase is operated at reduced pressure in the range of about 50 mm Hg to 700 mm Hg.

9. A process according to claim 2, 3, 4, 5, or 7 wherein the fermentor is operated at atmospheric pressure and said flashpot is operated at a reduced pressure in the range of 50 mm Hg to 500 mm Hg.

10. A process according to claims 1, 2, 3, 4, 5, or 7, wherein said distillation at reduced pressure is charged with a fermentation brew containing alcohol in the range of about 5 to 25% by weight and the pressure is in the range of about 50 to 150 mm Hg.

* * * * *